((12)) United States Patent
Sohngen et al.

(10) Patent No.: US 7,232,442 B2
(45) Date of Patent: Jun. 19, 2007

(54) HUMERAL NAIL

(75) Inventors: Gary W. Sohngen, San Pedro, CA (US); Dennis Scott Devinney, Tyler, TX (US)

(73) Assignee: Advanced Orthopaedic Solutions, San Pedro, CA (US)

( * ) Notice: Subject to any disclaimer, the term of this patent is extended or adjusted under 35 U.S.C. 154(b) by 109 days.

(21) Appl. No.: 11/063,151

(22) Filed: Feb. 22, 2005

(65) Prior Publication Data

US 2006/0200142 A1    Sep. 7, 2006

(51) Int. Cl.
  *A61B 17/56* (2006.01)
(52) U.S. Cl. ........................................ 606/62
(58) Field of Classification Search ............ 606/62–68
  See application file for complete search history.

(56) References Cited

U.S. PATENT DOCUMENTS

| | | | |
|---|---|---|---|
| 2,239,088 A * | 4/1941 | Ettinger .................... | 606/67 |
| 2,518,019 A | 8/1950 | Kane | |
| 3,433,220 A | 3/1969 | Zickel | |
| 4,622,959 A | 11/1986 | Marcus | |
| 4,776,330 A | 10/1988 | Chapman et al. | |
| 4,787,378 A * | 11/1988 | Sodhi .................... | 606/67 |
| 4,805,607 A | 2/1989 | Engelhardt et al. | |
| 4,827,917 A | 5/1989 | Brumfield | |
| 4,875,475 A | 10/1989 | Comte et al. | |
| 4,877,019 A | 10/1989 | Vives | |
| 4,946,459 A | 8/1990 | Bradshaw et al. | |
| 4,978,349 A | 12/1990 | Frigg | |
| 5,032,125 A | 7/1991 | Durham et al. | |
| 5,034,013 A | 7/1991 | Kyle et al. | |
| 5,041,115 A * | 8/1991 | Frigg et al. .................... | 606/62 |
| 5,074,882 A | 12/1991 | Grammont et al. | |
| 5,122,141 A | 6/1992 | Simpson et al. | |
| 5,127,913 A | 7/1992 | Thomas, Jr. | |
| 5,176,681 A | 1/1993 | Lawes et al. | |
| 5,201,735 A | 4/1993 | Chapman et al. | |
| 5,454,813 A | 10/1995 | Lawes | |
| 5,458,600 A | 10/1995 | Stapert et al. | |
| 5,489,284 A | 2/1996 | James et al. | |
| 5,505,733 A | 4/1996 | Justin et al. | |
| 5,505,734 A | 4/1996 | Caniggia et al. | |
| 5,549,610 A | 8/1996 | Russell et al. | |
| 5,569,249 A | 10/1996 | James et al. | |
| 5,620,445 A | 4/1997 | Brosnahan et al. | |
| 5,653,709 A | 8/1997 | Frigg | |
| 5,658,287 A | 8/1997 | Hofmann et al. | |

(Continued)

FOREIGN PATENT DOCUMENTS

JP    9066061    3/1997

(Continued)

*Primary Examiner*—Eduardo C. Robert
(74) *Attorney, Agent, or Firm*—Burgess Law Office, PLLC

(57) ABSTRACT

A nail for use with repairing a bone fracture. The nail includes a cutting tip formed of at least one facet defining a cutting edge. The facet is skewed with respect to a primary longitudinal axis extending through the nail from the proximal end to the distal end. The nail further includes at least one groove extending longitudinally on the nail from the distal end to the proximal end, the groove having a cutting edge used to increase or enlarge the entry opening as the diameter of the nail increases from the distal end to the proximal end.

21 Claims, 3 Drawing Sheets

U.S. PATENT DOCUMENTS

| | | |
|---|---|---|
| 5,704,939 A | 1/1998 | Justin |
| 5,766,174 A | 6/1998 | Perry |
| 5,855,579 A | 1/1999 | James et al. |
| 5,928,235 A | 7/1999 | Friedl |
| 5,935,127 A | 8/1999 | Border |
| 6,004,324 A | 12/1999 | Gahr et al. |
| 6,106,528 A | 8/2000 | Durham et al. |
| 6,228,086 B1 | 5/2001 | Wahl et al. |
| 6,261,290 B1 | 7/2001 | Friedl |
| 6,296,645 B1 * | 10/2001 | Hover et al. .................. 606/62 |
| 6,406,477 B1 | 6/2002 | Fujiwara |
| 6,648,889 B2 | 11/2003 | Bramlet et al. |

FOREIGN PATENT DOCUMENTS

| | | |
|---|---|---|
| WO | WO 94/13219 | 6/1994 |
| WO | WO 96/35387 | 11/1996 |

* cited by examiner

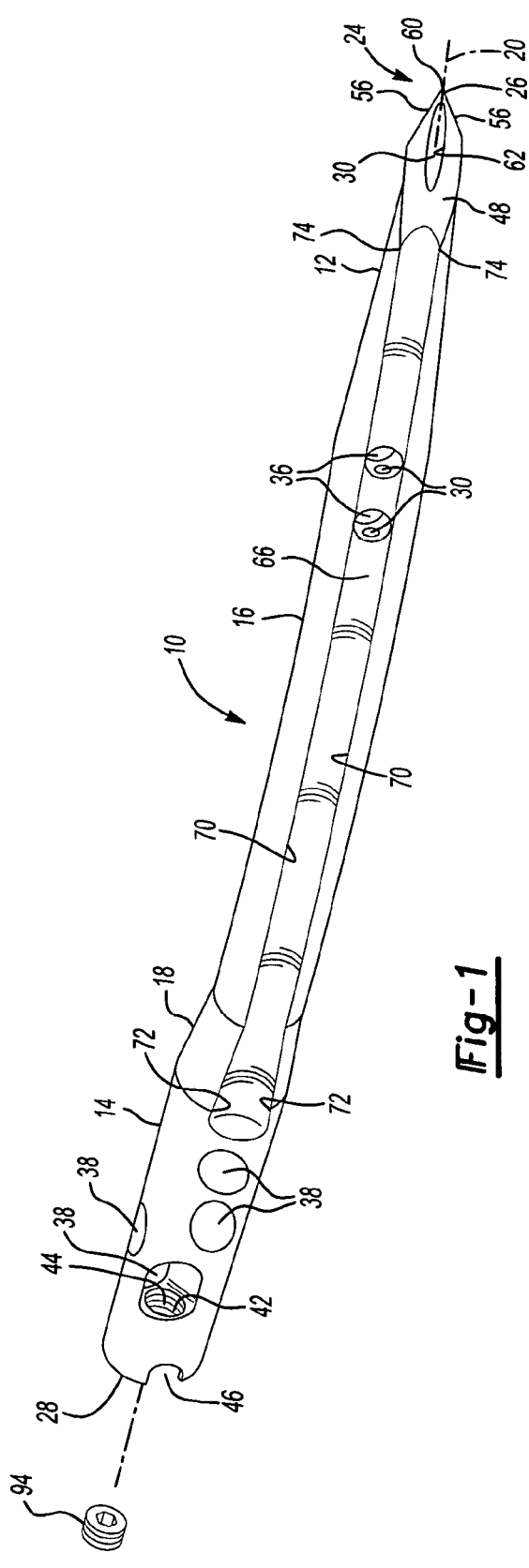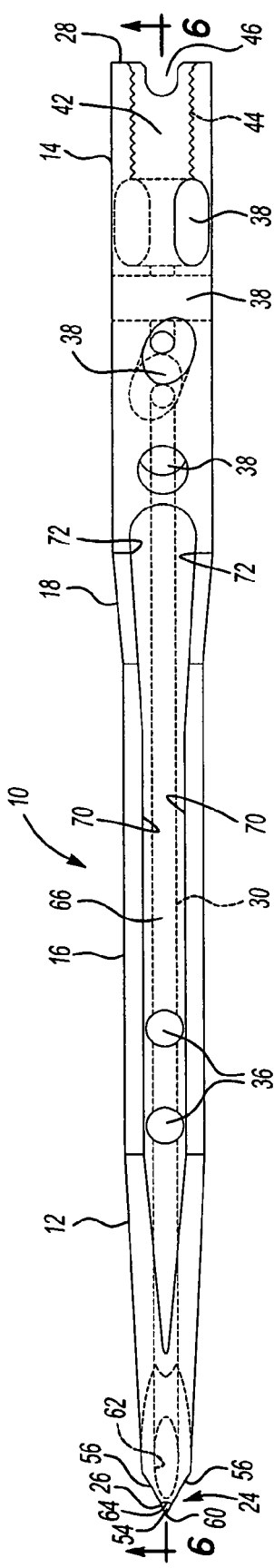

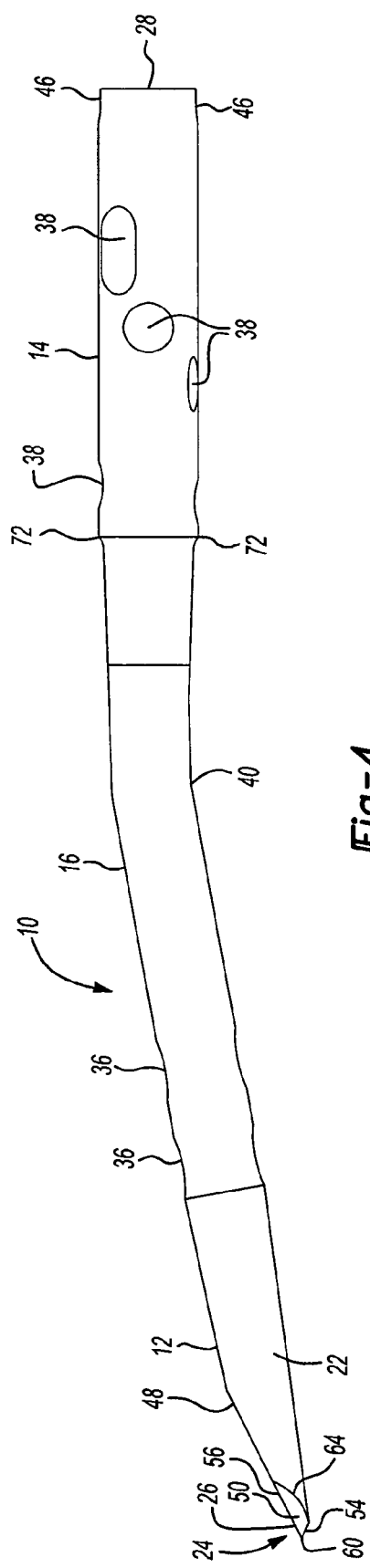
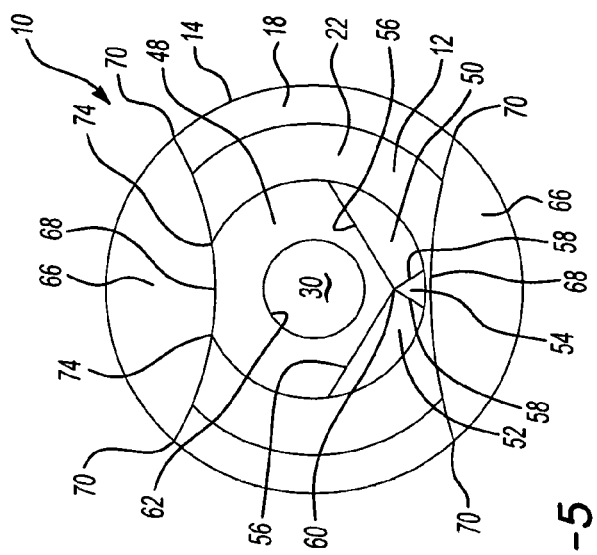
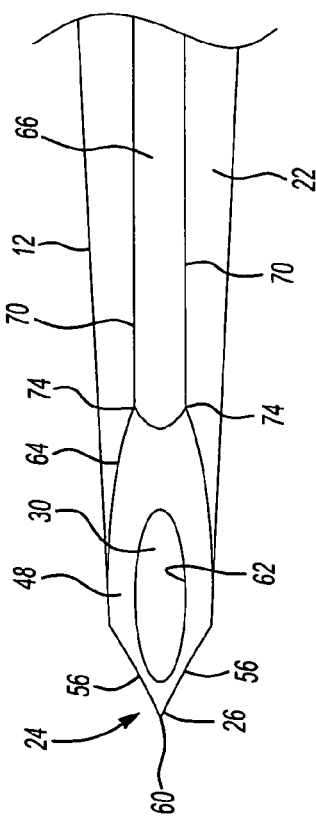

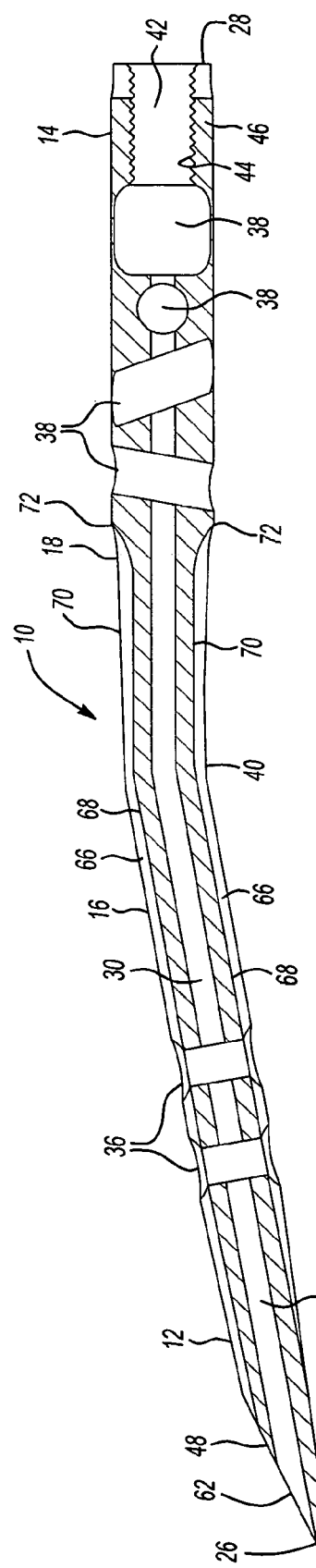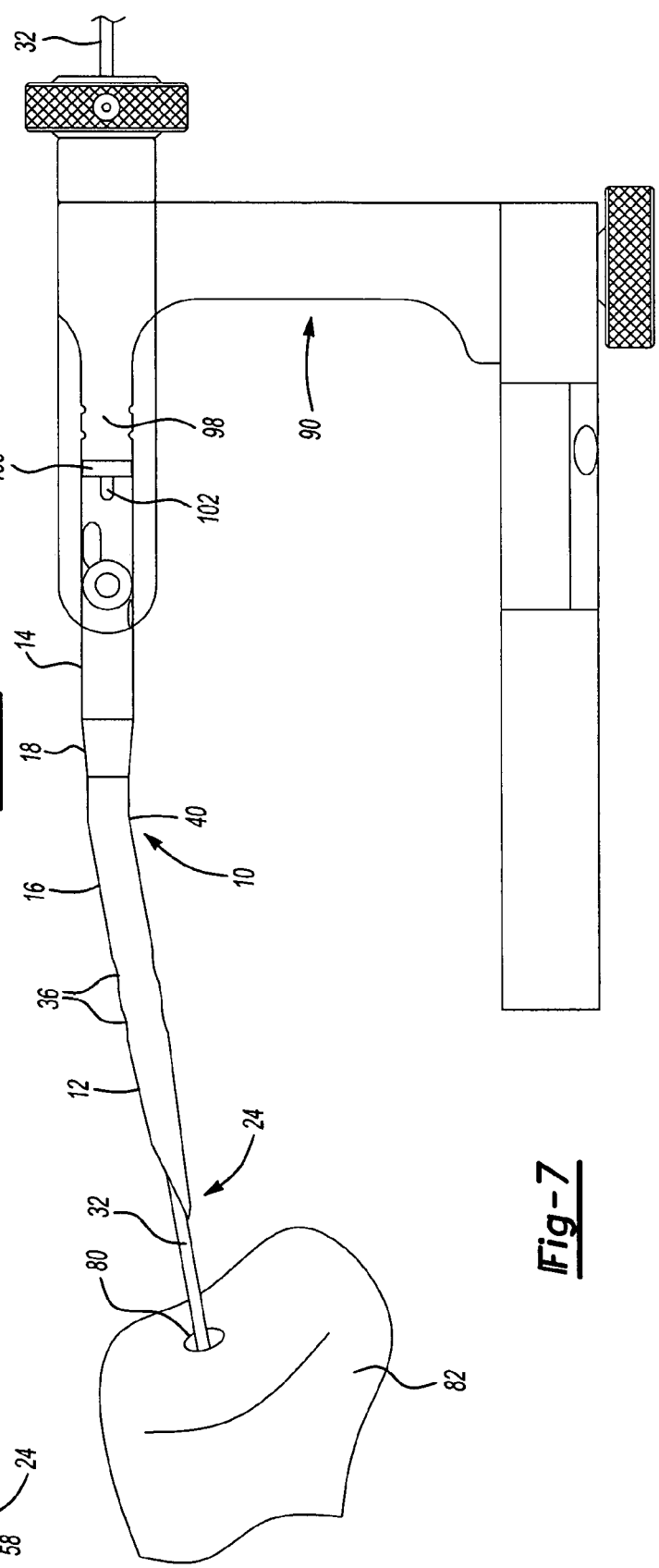

HUMERAL NAIL

CROSS-REFERENCE TO RELATED APPLICATIONS

Not applicable.

BACKGROUND OF THE INVENTION

1. Field of the Invention

The present invention relates generally to a fixation instrument for repairing bone fractures. More specifically, to a bone nail having a self entry feature.

2. Description of Related Art

Orthopedic fixation systems used for stabilizing a fracture often include an internal fixation device, typically an elongated implant such as a nail, screw or pin, inserted into the intramedullary canal of the bone to stabilize the fracture and promote healing. Humeral shaft fractures, like many bone fractures can be treated with a nail.

Typically a humeral nail is inserted into the humerus by first making an entry hole in the end thereof. The entry hole is made using either a drill or an awl to cut a hole, typically about 2 mm in diameter, in the cortical bone. Once an entry hole is made, a guide wire is inserted into the bone and extends through the entry hole into the bone past the fracture site. The guide wire helps to align the fracture.

A reamer is used to open the entry hole, along with the interior or intramedullary canal of the humerus, to form a passageway for the humeral nail. Typically the reamer opens a passageway in the cortical bone and the marrow space or intramedullary canal, approximately 1 to 1.5 millimeters larger than the overall diameter of the nail to be used. Once the reaming procedure is complete, the nail is attached to an insertion tool and is threaded over the guide wire. The nail is inserted into the bone, along the guide wire until it extends past and spans both sides of the fracture. Once the nail is properly aligned within the humerus, bone screws are inserted transversely through the bone and are received in openings or passageways located at or near the proximal and distal ends of the nail.

While reaming helps to open the bone and allow easier insertion of the humeral nail, it also requires an extra step. Further, in many cases if too much of the soft, spongy bone is removed, it may disrupt the blood supply within the humerus. Finally, if the entry hole and passageway has too great a diameter, the nail may move about within the interior of the bone.

SUMMARY OF THE INVENTION

Accordingly, the present invention is a bone nail for use in repairing a bone fracture. The nail includes a nail member having a primary longitudinal axis, a proximal end and a distal end. The proximal end including at least one aperture extending therethrough for receiving a fastener such as a bone screw. A longitudinal passageway extending through the nail member from the distal end to the proximal end. A cutting tip is located on the distal end of the nail member. The cutting tip having at least one facet, the facet skewed with respect to the primary longitudinal axis extending through the distal end of the nail member.

In an additional embodiment, at least one groove extends longitudinally along the nail member from the distal end toward the proximal end. The groove may include a cutting edge used to enlarge an entry hole in the bone as the nail increases in diameter from the diameter at the distal end to the diameter at the proximal end.

In another embodiment, the cutting tip has a plurality of facets, including a major facet and a plurality of minor facets. A cutting edge formed at an intersection of the major facet and one of the minor facets.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 1 of is a perspective view of a nail according to the present invention.

FIG. 2 as a front view of the nail of FIG. 1.

FIG. 3 is an enlarged rear view of the distal end of the nail of FIG. 1.

FIG. 4 is a side view of the nail of FIG. 1.

FIG. 5 is an end view of the distal end of the nail of FIG. 3.

FIG. 6 is a cross sectional side view of the nail of FIG. 1 taken along lines 6—6 of FIG. 2.

FIG. 7 is a perspective view of a nail according to the present invention shown attached to insertion equipment positioned adjacent the end of the humerus.

DETAILED DESCRIPTION OF THE PREFERRED EMBODIMENTS

FIGS. 1–5 illustrate a humeral nail or nail member 10 according to one embodiment of the present invention. The humeral nail 10 is formed of a metallic alloy such as a titanium alloy. The nail 10 includes a distal end 12, a proximal end 14 and a body or shank portion 16; a portion of which includes a tapered surface 18. The nail 10 includes a primary longitudinal axis 20. The distal end 12 includes a conically shaped portion 22 and a cutting tip 24 located at the leading or front end 26 of the nail 10. The proximal end 14 of the nail 10 includes a trailing or rear end 28.

A passageway 30 extends longitudinally, along the primary longitudinal axis 20, through the nail 10 between the leading end 26 of the distal end 12 and the trailing end 28 of the proximal end 14. The passageway 30 is sized to receive insertion and extraction instrumentation, seen generally at 90, including a guide wire 32, see FIG. 7, used to position the nail 10 within the bone 82. As discussed more fully herein, the leading end 26 of the nail 10 follows the path of the guide wire 32 and is inserted into the bone 82 first.

A plurality of apertures 36 are located near the distal end 12 of the nail 10. The apertures 36 typically extend transverse to the primary longitudinal axis 20 of the nail 10. In addition, the proximal end 14 of the nail 10 also includes a plurality of apertures 38. These apertures 38 extend either transverse to or at an angle with respect to the primary longitudinal axis 20 of the nail 10. In many instances, it is desirable to angle or skew the apertures 38 with respect to the primary longitudinal axis 20 of the nail 10 to account for any natural curvature of the bone. Thus, the apertures 38 remain substantially perpendicular to a longitudinal axis of the bone. In addition, the nail 10 has a slight bend or curvature 40, typically on the order of 10°, located on the body portion 16 of the nail 10 to once again compensate for any natural curvature of the bone 82 and facilitate entry of the nail 10 into the intramedullary canal of the bone 82.

A plurality of fasteners, such as bone screws (not shown), extend through the apertures 36, 38 located in the distal and proximal ends 12, 14 of the nail 10 and into the bone to secure both the distal end 12 and the proximal end 14 of the nail 10 in place once the nail is properly oriented in the bone. Other fasteners such as blades, beams, pins or wires could also be used to secure the nail 10 within the bone. p The proximal end 14 of the nail 10 also includes an aperture 42 extending inwardly from the trailing end 28 of the nail 10. The aperture includes a plurality of threads 44 that receive a threaded male member located on the insertion equipment 90. A pair of slots or notches 46 are located in the trailing end 28 of the proximal end 14. Insertion and extraction instruments 90, see FIG. 7 are used to rotate and properly position the nail 10 within the bone. An installation jig 98, including a collar 100 having a pair of projecting members 98 and a locking bolt (not shown) is positioned adjacent the trailing end of the nail 10. The projecting members 98 fit within the slots or notches 46 and the locking bolt extends through the collar 100 and is threadably received in the upper portion of the aperture 42. Prior to attaching the insertion and extraction instruments 90, the reduction screw 94 is threaded into the aperture 42 until it reaches the first aperture 38. This leaves the upper portion of the aperture 42 available to threadably receive the locking bolt. It should be understood that once the nail 10 is inserted and properly positioned in the bone and the insertion and extraction instruments 90 are removed, a threaded cap (not shown) may be placed in the threaded aperture 42 to protect it from bone ingrowth.

As illustrated in FIGS. 1–5, the cutting tip 24 includes a first or major face or facet 48. The cutting tip 24 further includes first, second and third minor faces or facets 50, 52, 54. Each face or facet 48, 50, 52, 54 extends at an angle with respect to the primary longitudinal axis 20 of the nail 10. The respective faces or facets 48, 50, 52, 54 converging together to form cutting edges at the intersection between each of the faces 48, 50, 52, 54. Specifically, major cutting edges 56 are formed between the first or major facet 48 and each of the first and second minor facets 50, 52. Minor cutting edges 58 are formed at the intersection of first and second minor facets 50, 52 with the third minor facet 54.

The major 56 and minor 58 cutting edges converge at a vertex or cutting point 60. The vertex or cutting point 60 is disposed on one side of the opening or aperture 62 in the major facet 48 created by the passageway 30. The two major cutting edges 56 form an obtuse angle at the vertex 60. Further, an acute angle is also formed between the each of the minor cutting edges 58. Additionally, the major cutting edges 54 lie on or are positioned substantially tangential or in close proximity to the opening 62 created by the passageway 30. In this arrangement, the opening 62 remains in the major facet 48.

Due to the planar nature of the major 48 and first, second and third 50, 52, 54 minor facets intersecting with the conically shaped portion 22 of the distal end 12 of the nail 10, the rear or trailing edges 64 of the facets 48, 50, 52, 54 formed at the outer periphery of the intersection between the major 48 and minor 50, 52, 54 facets and the conically shaped portion 22 surfaces is a curved or arcuate edge. While disclosed herein as planar, the major 48 and minor 50, 52, 54 facets may have a degree of curvature; i.e., be convex or concave surfaces or some combination thereof. In addition, the cutting edges 56, 58 may also have a degree of curvature.

In the disclosed embodiment, the nail 10 increases in diameter from the body or shank portion 16 to the proximal end 14. Thus, the nail 10 starts at the distal end 12 with the vertex 60. The conical section 22 increases gradually in diameter until it reaches the body or shank portion 16. The body or shank portion 16 remains a constant diameter until reaching the tapered surface 18 which is an outwardly beveled transitional surface extending between the body 16 and the proximal end 14 of the nail 10.

A pair of arcuate grooves 66 extend longitudinally on opposite sides of the nail 10. The grooves 66 are cut in the nail 10 at a standard depth or radius with respect to the body portion 16 of the nail 10. In the preferred embodiment, the degree of curvature or shape of the grooves 66 is a function of a radius extending from a point spaced a particular distance from the primary longitudinal axis 20 of the nail 10. Accordingly, the greater the radius, the shallower and wider the configuration of the grooves 66. One way to form the grooves 66 on the nail 10 is to insert the nail 10 longitudinally between a pair of spaced apart pinch mills. This is done prior to bending the nail 10. Thus, the size and curvature of the grooves 66 depends upon the radius of the opposing cutters of the pinch mills, the distance between the opposing cutters and the diameter of the nail 10.

In the preferred embodiment, the grooves 66 start in the conically shaped portion 22 located at the distal end 12. In the preferred embodiment, the groove 66 located on the same side of the nail 10 as the major face 48 starts after the opening 62 but prior to the rear or trailing edge 64 of the major face 48. The grooves 66 on the opposite side of the nail 10 starts roughly at the trailing edge 64 of the major facet 48, see FIG. 6. The depth of the grooves 66 gradually increases as the nail 10 increases in diameter along the conically shaped portion 22. Other than extending one of the grooves 66 a little further such that it extends into the major facet 48, the grooves 66 remain a constant size and depth as they extend along the nail body 16. As shown in FIG. 6, groove 66 on the major facet 48 side of the conical shaped portion 22 is milled a little bit deeper than the groove 66 located on the opposite side of the nail 10 whereby it extends into the major face 48 and forms cutting lands 74.

The grooves 66 increase in size as they extend through the tapered surface 18 of the nail 10 and ultimately into the proximal end 14 of the nail 10. The increase results from the increase in diameter of the nail 10 through the tapered surface 18 and the proximal end 14. As the grooves 66 extend to the tapered surface a form an additional pair of cutting lands 72 that are raised slightly above the cutting edge 70 of the grooves 66 such that they provide aid cutting surface that facilitates insertion of the nail 10 as it travels through the bone 82 from the tapered section 18 to the proximal end 14.

In the preferred embodiment, other than the area of the groove 66 adjacent the major facet 48, the bottom or lower surface 68 of each groove 64 is spaced a constant distance from and remains substantially parallel to the passageway 30. Each of the grooves 66 also includes a pair of longitudinally extending opposed cutting 70 edges extending from the conically shaped portion 22 to the proximal end 14.

Alternative embodiments of the nail 10 may include a different number of facets located at the cutting tip 24. In addition, the number of grooves 60 may vary, along with the depth and length thereof.

The nail 10 of the present invention is typically inserted into a humeral bone of patient using a suitably known technique. Generally, an entry hole or aperture 80, approximately 2 mm in diameter, is drilled or formed with an awl in the end of the humerus 82. A 2 mm guide wire 32 is inserted through the entry hole until it extends past and spans the location of the fracture. The nail 10 is attached to the insertion equipment or insertion guide instrument 90, typically a L-shaped member having an insertion jig 98 including a collar 100 having a pair of projecting members 102. A locking bolt extends through the collar 100 and engages the threads 44 on the proximal end 14 of the nail 10. Accordingly, tightening the locking bolt secures the insertion equipment 90 to the nail 10. As set forth previously, the reduction screw 94 is threadably received in the aperture 42 prior to attaching the insertion instrument 90 to the nail 10.

The nail 10 is placed over the guide wire 32 and slid along the guide wire 32 until the vertex 60 of the cutting tip 24 of the nail 10 engages the bone. The cutting edges 56, 58 along with the facets 48–54 function together to form self cutting entry tip that enlarges the entry hole 80 in the bone 82 as the nail 10 is be inserted into the bone 82 and the corresponding intramedullary canal thus eliminating the need for a reamer or drill to enlarge the entry hole 80 in the cortical bone. As part of the insertion procedure, the surgeon using the insertion equipment 90 rotates the nail 10 about the primary longitudinal axis 20. In addition, the surgeon applies an impact load or force to the end of the insertion equipment 90 to drive the nail 10 through the cortical bone and into the intramedullary canal. Accordingly, the facets 48–54 and cutting edges 56, 58 cooperate together to enlarge the entry hole 80 and permit entry of the nail 10 without the need for a separate reaming step.

The grooves 66 provide a twofold function. Initially, they provide a void or space that helps remove the cortical bone chips cut by the cutting edges 56, 58. Further, the opposed cutting edges 70 of the grooves 66 also engage and cut away the cortical bone, when the nail 10 is rotated, to enlarge the entry hole 80 such that as the nail 10 increases in diameter from the distal diameter to the proximal diameter, the nail 10 can be fully inserted into the intramedullary canal. In addition to the cutting edges 70 of the grooves 66, the grooves 66 may also include cutting lands 72 and 74 located at the respective ends of the grooves 66. These cutting lands 72, 74 provide an additional cutting face or surface to further remove cortical bone as the nail 10 is inserted into the bone 82.

Accordingly, as the nail 10 increases in diameter in the conical section 22 and in the tapered surface 18, between the body 16 of the nail 10 and the proximal end 14, the cutting edges 70 of the grooves 64, along with the cutting lands 72, 74 function to cut away cortical bone to enlarge the entry hole 80. Once the position of the nail 10 is confirmed by conventional image intensification techniques, the guide wire 32 is removed and the bone screws are inserted to secure and anchor the nail 10 within the humerus. Once the insertion instrument 90 is removed, the surgeon may insert a suitable tool into the drive socket located on the reduction screw 94 to rotate the reduction screw 94 such that it engages the bone screw extending through the aperture 38. As the first or uppermost aperture 38 is elongated, continued rotation of the reduction screw 94 will draw the distal end 12 of the nail 10 closer thus reducing span of the fracture by bringing the respective fractured portions together.

The design of the present invention provides a nail 10 that can be inserted through the cortical bone and into the intramedullary canal without using a separate reamer to either enlarge the entry hole in the cortical bone or to ream or enlarge a passageway in the intramedullary canal of the bone.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A nail for use with repairing a bone fracture comprising:
   a nail member, said nail member having a primary longitudinal axis, a proximal end and a distal end, said proximal end including at least one aperture extending therethrough for receiving a fastener, at least one aperture extending through said nail near said distal end for receiving a fastener, said nail member further having a longitudinal passageway extending from said distal end to said proximal end;
   a cutting tip located on said distal end of said nail member, said cutting tip having at least one facet, said facet skewed with respect to said primary longitudinal axis extending through said distal end, said passageway extends to and forms an opening in said facet, said opening located entirely on said facet; and
   a cutting edge, said cutting edge a part of a leading end of said nail member.

2. A nail for use with repairing a bone fracture as set forth in claim 1 wherein said facet is a planar surface disposed at an acute angle with respect to the primary longitudinal axis of the nail.

3. A nail for use with repairing a bone fracture as set forth in claim 1 wherein said cutting tip includes a plurality of facets.

4. A nail for use with repairing a bone fracture as set forth in claim 3 wherein said plurality of facets includes a major facet and a minor facet.

5. A nail for use with repairing a bone fracture as set forth in claim 3 wherein said plurality of facets includes a major facet and first, second and third minor facets.

6. A nail for use with repairing a bone fracture comprising:
   a nail member, said nail member having a primary longitudinal axis, a proximal end and a distal end, said proximal end including at least one aperture extending therethrough for receiving a fastener, at least one aperture extending through said nail near said distal end for receiving a fastener, said nail member further having a longitudinal passageway extending from said distal end to said proximal end;
   a cutting tip located on said distal end of said nail member, said cutting tip having at least one facet, said facet skewed with respect to said primary longitudinal axis extending through said distal end;
   a cutting edge, said cutting edge as part of a leading end of said nail member;
   wherein said cutting tip includes a plurality of facets;
   wherein said plurality of facets includes a major facet and a minor facet; and
   including a cutting edge formed at an intersection of said major and at least two of said minor facets.

7. A nail for use with repairing a bone fracture comprising:
   a nail member, said nail member having a primary longitudinal axis, a proximal end and a distal end, said proximal end including at least one aperture extending therethrough for receiving a fastener, at least one aperture extending through said nail near said distal end for receiving a fastener, said nail member further having a longitudinal passageway extending from said distal end to said proximal end;

a cutting tip located on said distal end of said nail member, said cutting tip having at least one facet, said facet skewed with respect to said primary longitudinal axis extending through said distal end;

a cutting edge, said cutting edge as part of a leading end of said nail member;

wherein said cutting tip includes a plurality of facets;

wherein said plurality of facets includes a major facet and first, second and third minor facets; and including a cutting edge formed at an intersection of said major facet and said first minor facet, at an intersection of said major facet and said second minor facet and at an intersection of said first minor facet with said third minor facet and at an intersection of said second minor facet with said third minor facet.

8. A nail for use with repairing a bone fracture as set forth in claim 7 wherein said passageway extends to and forms an opening in said major facet.

9. A nail for use with repairing a bone fracture as set forth in claim 7 wherein said cutting edges converge at a vertex.

10. A nail for use with repairing a bone fracture as set forth in claim 9 wherein said vertex is disposed on one side of an opening in said major facet, said opening created by said passageway ending at said major facet.

11. A nail for use with repairing a bone fracture as set forth in claim 10 wherein the cutting tip includes at least two major cutting edges forming an obtuse angle at the vertex, said major cutting edges lying in close proximity to the opening.

12. A nail for use with repairing a bone fracture as set forth in claim 7 including at least one groove extending longitudinally on said nail.

13. A nail for use with repairing a bone fracture as set forth in claim 12 wherein said groove includes at least one cutting edge.

14. A nail for use with repairing a bone fracture comprising:

a nail member, said nail member having a primary longitudinal axis, a proximal end and a distal end, said proximal end including at least one aperture extending therethrough for receiving a fastener, said nail member further having a longitudinal passageway extending from said distal end to said proximal end;

a cutting tip located on said distal end of said nail member, said cutting tip having a plurality of facets including a major facet and first, second and third minor facets;

a cutting edge formed at an intersection of said major facet and said first minor facet, at an intersection of said major facet and said second minor facet, at an intersection of said first minor facet with said third minor facet and at an intersection of said second minor facet with said third minor facet; and at least one groove extending longitudinally on said nail from said distal end towards said proximal end.

15. A nail for use with repairing a bone fracture as set forth in claim 14 wherein said cutting edges converge at a vertex.

16. A nail for use with repairing a bone fracture as set forth in claim 14 wherein said groove includes at least one cutting edge.

17. A nail for use with repairing a bone fracture as set forth in claim 15 wherein said the vertex is disposed on one side of an opening located in said major facet created by said passageway, said opening created by said passageway ending at said major facet.

18. A nail for use with repairing a bone fracture as set forth in claim 17 wherein the cutting point includes at least two major cutting edges forming an obtuse angle at the vertex, the major cutting edges lying in close proximity to the opening.

19. A method for installing a nail in a bone to repair a fracture comprising the steps of:

forming an entry hole in the end of the bone;

inserting a guide wire through the entry hole into the bone until it extends past and spans the location of the fracture;

attaching a nail to insertion equipment, said nail having a primary longitudinal axis, a proximal end and a distal end, said proximal end including at least one aperture extending therethrough for receiving a fastener, said nail further having a longitudinal passageway extending from said distal end to said proximal end, said nail having a cutting point including a major facet and at least one minor facet, a cutting edge formed at an intersection of said major facet and said minor facet;

placing the nail over the guide wire such that the guide wire extends through at least a portion of the longitudinal passageway in the nail; and moving the nail along the guide wire until the cutting tip engages the bone and rotating the nail, whereby the cutting edge and facets function together to enlarge the entry hole in the bone whereby the nail can be inserted into an intramedullary canal of the bone.

20. A method for installing a nail in a bone to repair a fracture as set forth in claim 19 including:

providing the cutting tip with a plurality of facets including a major facet and first, second and third minor facets, a cutting edge formed at an intersection of said major facet and said first minor facet, at an intersection of said major facet and said second minor facet, at an intersection of said first minor facet with said third minor facet and at an intersection of said second minor facet with said third minor facet; and providing said nail with at least one groove extending longitudinally on said nail from said distal end towards said proximal end, the groove having a cutting edge, whereby rotation of the nail enlarges the entry hole as the nail is inserted as the diameter of the nail increases from the distal end to the proximal end.

21. A nail for use with repairing a bone fracture comprising:

a nail member, said nail member having a primary longitudinal axis, a proximal end and a distal end, said proximal end including at least one aperture extending therethrough for receiving a fastener, at least one aperture extending through said nail near said distal end for receiving a fastener, said nail member further having a longitudinal passageway extending from said distal end to said proximal end;

a cutting tip located on said distal end of said nail member, said cutting tip having at least one facet, said facet skewed with respect to said primary longitudinal axis extending through said distal end, said passageway extends to and forms an opening in said cutting tip, said cutting tip having a vertex, said vertex spaced from said opening in said cutting tip; and a cutting edge, said cutting edge a part of a leading end of said nail member.

* * * * *